(12) United States Patent
Mangiardi

(10) Patent No.: US 8,608,650 B2
(45) Date of Patent: Dec. 17, 2013

(54) SURGICAL ACCESS INSTRUMENTS FOR USE WITH DELICATE TISSUES

(75) Inventor: John R. Mangiardi, Greenwich, CT (US)

(73) Assignee: Vycor Medical, LLC, Boca Raton, FL (US)

( * ) Notice: Subject to any disclaimer, the term of this patent is extended or adjusted under 35 U.S.C. 154(b) by 362 days.

(21) Appl. No.: 12/545,686

(22) Filed: Aug. 21, 2009

(65) Prior Publication Data

US 2010/0010315 A1 Jan. 14, 2010

Related U.S. Application Data

(63) Continuation of application No. 11/155,175, filed on Jun. 17, 2005, now abandoned.

(51) Int. Cl.
*A61B 1/00* (2006.01)

(52) U.S. Cl.
USPC .......................................................... 600/184

(58) Field of Classification Search
USPC .................... 600/114, 184, 201, 210, 215;
604/164.01, 164.09, 164.1, 165.01,
604/165.02, 165.04, 166.01, 170.01,
604/170.02; 606/108, 191, 197, 199, 114,
606/184, 201, 210, 215
See application file for complete search history.

(56) References Cited

U.S. PATENT DOCUMENTS

| | | | |
|---|---|---|---|
| 2,769,411 A | | 11/1956 | Abramson |
| 2,769,441 A | | 11/1956 | Abramson |
| 2,922,415 A | * | 1/1960 | Campagna .................... 600/184 |
| 3,417,746 A | * | 12/1968 | Moore et al. .................. 600/184 |
| 3,626,471 A | | 12/1971 | Florin |
| 3,766,910 A | | 10/1973 | Lake |
| 3,882,855 A | | 5/1975 | Schulte et al. |
| 3,888,117 A | | 6/1975 | Lewis |
| 4,263,900 A | | 4/1981 | Nicholson |
| 4,312,353 A | | 1/1982 | Shahbabian |

(Continued)

FOREIGN PATENT DOCUMENTS

| JP | 05-344978 | 12/1993 |
|---|---|---|
| JP | 9-224943 | 9/1997 |

(Continued)

OTHER PUBLICATIONS

Hilton, et al. "METRx Microdiscectomy Surgical Technique," Medtronic Sofamor Danek publication, 2001, 20 pages.

(Continued)

*Primary Examiner* — Thomas McEvoy
(74) *Attorney, Agent, or Firm* — RatnerPrestia

(57) ABSTRACT

Surgical instruments providing access to delicate tissue, such as brain tissue or breast tissue, through a transcutaneous incision. A surgical apparatus may have a hollow sleeve retractor extending along a longitudinal axis from a proximal retractor end to a distal retractor end and an introducer having a proximal introducer end and a distal introducer end. The proximal introducer end is configured to install within the hollow sleeve with its distal end extending beyond the distal retractor end. The distal introducer end is tapered and may have a rounded profile in a plane parallel to the longitudinal axis to displace delicate brain tissue transversely to the longitudinal axis without damage to the tissue. The distal retractor end may be blunt and adapted to support adjacent brain tissue while minimizing disruption to the tissue after the retractor is positioned at a surgery site and the introducer is removed from the retractor.

18 Claims, 11 Drawing Sheets

(56) References Cited

U.S. PATENT DOCUMENTS

| | | |
|---|---|---|
| 4,502,468 A | 3/1985 | Burgin |
| 4,636,199 A | 1/1987 | Victor |
| 4,931,039 A | 6/1990 | Coe et al. |
| 4,945,896 A | 8/1990 | Gade |
| 5,052,373 A | 10/1991 | Michelson |
| 5,135,526 A * | 8/1992 | Zinnanti et al. ............... 606/49 |
| 5,160,323 A | 11/1992 | Andrew |
| 5,249,568 A | 10/1993 | Brefka et al. |
| 5,275,583 A | 1/1994 | Crainich |
| D377,093 S | 12/1996 | Michelson |
| 5,782,807 A | 7/1998 | Falvai et al. |
| 5,785,648 A | 7/1998 | Min |
| 5,792,044 A | 8/1998 | Foley et al. |
| 6,093,145 A | 7/2000 | Vom Berg et al. |
| 6,096,038 A | 8/2000 | Michelson |
| 6,142,931 A * | 11/2000 | Kaji ............................ 600/114 |
| 6,156,054 A | 12/2000 | Zadno-Azizi et al. |
| 6,221,078 B1 | 4/2001 | Bylsma |
| 6,224,599 B1 | 5/2001 | Baynham et al. |
| 6,296,647 B1 | 10/2001 | Robioneck et al. |
| 6,371,964 B1 | 4/2002 | Vargas et al. |
| 6,383,191 B1 | 5/2002 | Zdeblick et al. |
| 6,425,859 B1 | 7/2002 | Foley et al. |
| 6,461,330 B1 | 10/2002 | Miyagi |
| 6,565,574 B2 | 5/2003 | Michelson |
| 6,589,211 B1 | 7/2003 | MacLeod |
| 6,595,917 B2 | 7/2003 | Nieto |
| 6,599,292 B1 | 7/2003 | Ray |
| 6,761,687 B1 * | 7/2004 | Doshi et al. ................. 600/184 |
| D495,053 S | 8/2004 | Laun |
| 6,863,674 B2 | 3/2005 | Kasahara et al. |
| 6,896,680 B2 | 5/2005 | Michelson |
| 7,081,089 B2 | 7/2006 | Bonadio et al. |
| 7,153,304 B2 | 12/2006 | Robie et al. |
| 7,235,084 B2 | 6/2007 | Skakoon et al. |
| 7,474,820 B2 | 1/2009 | Vayser et al. |
| 7,510,524 B2 | 3/2009 | Vayser et al. |
| 7,686,492 B2 | 3/2010 | Vayser et al. |
| 2001/0010002 A1 | 7/2001 | Michelson |
| 2002/0151769 A1 | 10/2002 | Kim |
| 2002/0161366 A1 | 10/2002 | Robie et al. |
| 2004/0097792 A1 | 5/2004 | Moll et al. |
| 2004/0230100 A1 | 11/2004 | Shluzas |
| 2005/0273132 A1 | 12/2005 | Shluzas et al. |
| 2005/0277811 A1 | 12/2005 | Richards et al. |
| 2006/0122462 A1 | 6/2006 | Roth et al. |
| 2008/0109026 A1 | 5/2008 | Kassam |

FOREIGN PATENT DOCUMENTS

| | | |
|---|---|---|
| JP | 2000-287915 | 10/2000 |
| JP | 200287915 A | 10/2000 |
| JP | 2003-153907 | 5/2003 |
| RU | 45928 | 6/2005 |
| RU | 55570 | 8/2006 |
| SU | 131027 | 3/1959 |
| SU | 1521465 | 11/1989 |
| WO | WO 2001/043627 | 6/2001 |
| WO | WO 2006/017507 | 2/2006 |
| WO | WO 2006/050047 | 5/2006 |

OTHER PUBLICATIONS

Kelly, et al. "The stereotaxic retractor in computer-assisted stereotaxic microsurgery," Journal of Neurosurgery, vol. 69, Aug. 1988, pp. 301-307, 7 pages.

Alexander, et al. "Chapter 20: Stereotactic Frame Systems: The COMPASS System," Advanced Neurosurgical Navigation, 1999, pp. 267-277. 13 pages.

Engh, et al. NeuroendoportSM surgery facilitates removal of hard-to-reach brain tumors, University of Pittsburgh Neurosurgery News, vol. ,10, No. 2, 2009. 8 pages.

Raza,et al. "Minimally Invasive Trans-Portal Resection of Deep Intracranial Lesions," Minimally Invasive Neurosurgery, vol. 54, Feb. 2011, pp. 1-7.

Recinos, et al. "Use of a minimally invasive tubular retraction system for deep-seated tumors in pediatric patients," Journal of Neurosurgery: Pediatrics, vol. 7, May 2011, pp. 516-521. 6 pages.

Prevedello, et al. "Vycor ViewSite TC: Endoscope guided Intraparenchimal Brain Tumor Ressection," Ohio State University Medical Center Minimally Invasive Neurosurgery, 2 pages.

Shults, et al. "Neuro-Opthalmic Complications of Intracranial Catheters," Neurosurgery, vol. 33, No. 1, Jul. 1993, pp. 135-138. 4 pages.

Greenfield, et al. "Stereotactic Minimally Invasive Tubular Retractor System for Deep Brain Lesions," Operative Neurosurgery 2, vol. 63, Oct. 2008, pp. 334-340. 7 pages.

Extended European Search Report for EP 06 840 022.5, The Hague, Mar. 18, 2013.

Decision for Rejection for Patent Application No. 2009-539227 dated May 31, 2013.

* cited by examiner

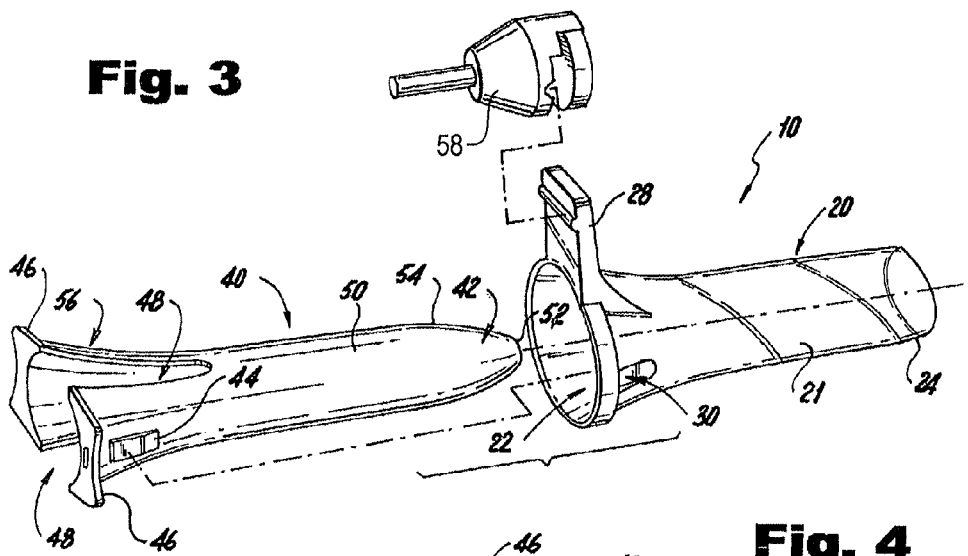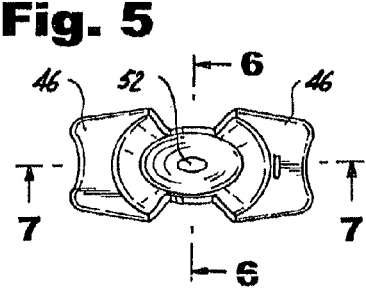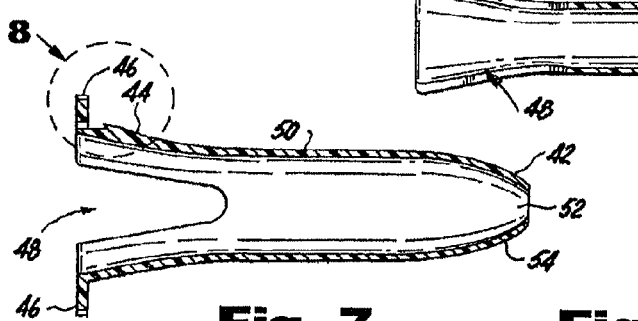

SURGICAL ACCESS INSTRUMENTS FOR USE WITH DELICATE TISSUES

CROSS REFERENCE TO RELATED APPLICATIONS

This application is a continuation of U.S. patent application Ser. No. 11/155,175 filed Jun. 17, 2005 now abandoned, which application is incorporated herein by reference in its entirety.

FIELD OF INVENTION

This disclosure relates to surgical access instruments for use with delicate tissues and methods of use.

BACKGROUND

Traditional surgical brain retractors are thin, firm or malleable bands of steel or other metal alloys, with abrupt or well-defined edges and have limited surface areas. The common structural form of the standard retractor is a simple strip of metal consisting of a metal strip which can be bent by hand and the surface of which typically is used to pull apart or spread delicate tissue. The strip typically is clearly outlined on the brain after a few minutes, and particularly noticeable are the pressure marks from the lateral spatula edges which indicate a high local compression stress. These traditional retractors can be introduced into the tissue of the brain or along brain surfaces, and then pulled with force to either separate or elevate the brain tissue during surgery. This method allows the target area to be illuminated and visualized in order to perform the surgical procedure. However, brain tissue is quite soft and delicate, particularly after trauma, loss of blood supply, or in the presence of brain edema. The brain tissue is a gel-like substance that can be easily damaged, and a complication known as "retraction injury" can occur, sometimes resulting in compromised brain function. The brain tissues can be torn by the relatively sharp edges of these retractors, and/or the retracted brain can lose blood supply when the local pressure beneath the retractor is greater than venous pressure. The result can be ischemic changes in the underlying brain and/or the more serious complication of venous brain infarction.

The combination factors including the softness of the brain tissue, and the effects of sharp, blunt edges and limited surface area of traditional metal band retractor also results in limited visualization of the surgical target area. The brain tends to extend beyond or "droop" around the edges of the retractor, limiting the area necessary for lighting and reducing overall visibility.

Furthermore, the amount of local pressure exerted by the retractor on the brain tissue must be limited to avoid injury, which may impede the surgeon's ability to safely gain enough visualization area. Oftentimes, the surgeon will resort to the strategy of exposing far more of the brain tissue than is necessary or desirable to open the area around the brain widely enough so as to limit the amount of local retraction pressure. This method is undesirable, as compared to a less invasive approach, for both the patient and surgeon.

It would be advantageous to provide a surgical instrument assembly that safely addresses the shortcomings of the presently-known instruments.

EXEMPLARY OBJECTS OF THE INVENTION

Exemplary objects and design principles of the surgical access instrument assemblies of this invention are as follows:

(1) to maximize surface area of the retractor, so as to distribute pressure evenly and minimize effective local retraction pressure or specific high pressure points;
(2) to enable integration with stereotactic neuro-navigation computer guidance system;
(3) to reduce the need to "pull" on a brain retractor, to obviate the possibility of accidental over-retraction and thereby avoid brain damage;
(4) to allow for binocular vision with the utilization of elliptical architecture;
(5) to allow for maximal lighting access clearance and target tissue visualization;
(6) to allow for minimization of brain disruption by limiting the corticotomy via use of a small elliptical window for the transcortical introducer;
(7) to allow for minimization of brain disruption with the utilization of tapered forward edges;
(8) to enable stable retraction fixation to avoid accidental retractor displacement;
(9) to provide retractors which are of lightweight materials to allow for ease of manipulation; and/or,
(10) to provide transparent retractors to allow for direct visualization of underlying brain tissue.

Other objects also may become apparent from the following description of the present invention.

SUMMARY OF THE INVENTION

In keeping with these objects and others which may become apparent, the present invention is directed toward an access assembly for surgical instruments. Non-limiting, exemplary embodiments of the access assembly are described in this Summary of the Invention and elsewhere herein. The access assembly for surgical instruments includes two principal components. One component is an internal instrument access assembly and the other is an external instrument access assembly. The internal instrument access assembly is designed to enter the brain to gain access to deeper internal brain structures. The external instrument access assembly is designed to separate or elevate the surfaces of the brain to gain access to external structures along, around or beneath the brain. Both will be produced in varying sizes according to the needs of individual operations. The materials for these retractors will be composed of transparent biocompatible lightweight plastic. Each of the instrument assemblies includes two separate parts: a retractor that also functions as a working channel, and a compatible introducer.

The internal instrument assembly is a wedge retractor introducer, which preferably includes a hollow wedge formed by all or part of a closed curve in cross section, such as an elliptical rounded wedge or an arch shaped wedge. It includes a hollow brain access working channel that can be fixed in space to a standard neurosurgical fixation cable device. First, a protruding introducer element, having a length greater than the length of the hollow working channel, is introduced into the working channel. Its distal smooth and relatively soft tapered end works to spread apart the brain hemispheres or other portions of delicate brain tissue. When the working channel is introduced, the introducer is removed, leaving the hollow working channel for the surgeon to access to the target tissues. Variations will include length (Z axis), and width and height (X and Y axes) of the elliptical working channel and introducer.

A fixation portion is designed to be attached to a standard neurosurgical armature fixation device.

The external surgical access instrument assembly is characterized by an arched hemi-elliptical architecture, wider along the base (X axis) than tall (Y axis). It is smooth, tapered at the leading edge, has a handle fixation portion that is o the same design as that of the internal instrument assembly, and is designed to be attached to a standard neurosurgical armature fixation device. Variations will be in length (Z axis) as well in X and Y axes.

Therefore, the present invention encompasses one or more surgical instrument assemblies to provide access to delicate tissue at the end of the working channel, such as brain tissue or breast tissue, through a transcutaneous incision, for a variety of reasons, such as to access a surgical site; to provide access to insert an inflatable prosthesis; or to provide access for providing an external buttress channel for supporting tissue thereon. The surgical instrument assembly includes an interleaved combination of an open sleeve hollow retractor and a tapered tipped wedge introducer. The wedge introducer is introduced into an area adjacent to the hollow sleeve. The distal tip of the wedge introducer extends beyond a distal end of the hollow retractor, forward of a distal end of said hollow retractor, so that the wedge introducer traverses the delicate tissue ahead of the distal end of the hollow retractor, guiding the hollow retractor into place in the delicate tissue.

When used in conjunction with working surgical instruments, the distal end of the introducer has a small opening, preferably elliptically oval, to allow for removal of small portions of tissue from a surgical site.

The hollow retractor may have a diameter which is a closed curve, such as an elliptical oval. In such case, a tapered tipped wedge introducer is inserted into the inside of the closed curved hollow retractor. In an alternate embodiment, the tapered tipped wedge introducer may have a diameter which is an arc, wherein the arc is a portion of a closed curve, and further wherein the tapered tipped wedge is an arch insertable into the closed curved hollow retractor.

When used as an external working channel, the distal end of the working channel is bell shaped, to allow for increase for increased surface area exposure.

The hollow retractor may alternatively also be an arc of a portion of a closed curve, also forming an arch shape. In such case, the tapered curved tipped wedge introducer may also be an arc of a portion of a closed curve, also forming an arch shape.

In the case where the hollow retractor and/or the tapered tipped wedge introducer has a diameter of at least one arc of a curve, they preferably can have a decreasing curved cross sectional diameter.

Moreover, in such case where the hollow retractor is arch shaped, as opposed to being a closed curved shape, such as being an-elliptical oval in cross section, the wedge introducer is placed adjacent to the concave inner portion of the hollow retractor.

If the hollow retractor is a closed curve, that is, having an elliptical oval cross section, preferably of decreasing diameter towards it distal, tissue contact edge, then the combination of the hollow retractor and wedge introducer are used to either spread apart adjacent delicate tissues, such as the left and right hemispheres of the brain, or to traverse the delicate tissue, such as brain tissue, to provide internal access to a surgical site within the delicate tissue.

If the hollow retractor is arch-shaped, that is, having a diameter which is an arc, namely, a portion of a closed curve, then the combination of the hollow retractor and the wedge introducer are used to provide access to a delicate tissue, where the delicate tissue is supported upon the convex outer surface of the hollow retractor, forming a support buttress, after removal of the arch-shaped wedge introducer.

Additionally, if the hollow retractor is also arch-shaped, that is, having a diameter which is an arc, namely, a portion of a closed curve, then additionally the combination of the hollow retractor and the wedge introducer is used to provide access to a delicate tissue, where an inflatable member, such as a breast prosthesis, is inserted into the delicate breast tissue and inflated, after removal of the arch-shaped wedge introducer from the hollow arched retractor.

The tipped wedge introducer has an exterior surface corresponding to an interior Surface of the hollow sleeve and the closed end tipped wedge introducer may have a diameter with an arc of a decreasing curved cross section approximating the arc of the curved cross section of the open sleeve of the retractor.

Preferably, the retractor includes a handle or a tab that is attachable to a clamp.

Optionally, the hollow retractor and the tapered tipped wedge introducer include a lock temporarily locking said tapered tipped wedge introducer adjacent to the hollow retractor.

When the hollow retractor is elliptically oval in cross section, the closed plane curve is generated by a point moving in such a way that the sums of its distances from two fixed points is a constant, or the closed plane curve is a plane section of a circular cone that is a not perpendicular to an axis of the cone, thereby forming a planar elliptical oval slice through the cone.

Moreover, the hollow retractor may be flared at a proximal end. Additionally, where a base of a handle is attached, the handle may merge in a cascading shape, interrupting the continuous curve of the proximal end of the hollow retractor. Such a cascading dip in structure allows for easier finger access into the working channel of the hollow retractor.

Additionally, the hollow retractor may have a changing cross section, where the cross sectional diameter of the elliptical oval is wider or narrower at selected regions of the working channel of the hollow retractor.

DESCRIPTION OF THE DRAWINGS

The present invention can best be understood in connection with the accompanying drawings. It is noted that the invention is not limited to the precise embodiments shown in drawings, in which:

FIG. 3 shows exploded components of FIG. 2.

FIG. 4 is a top plan view of an introducer.

FIG. 5 is a proximal end view of an introducer.

FIG. 6 is a side sectional elevational view thereof.

FIG. 7 is a top plan sectional view thereof.

FIG. 8 is a sectional detail of a locking tab, taken from FIG. 7.

DETAILED DESCRIPTION

Figure 1:
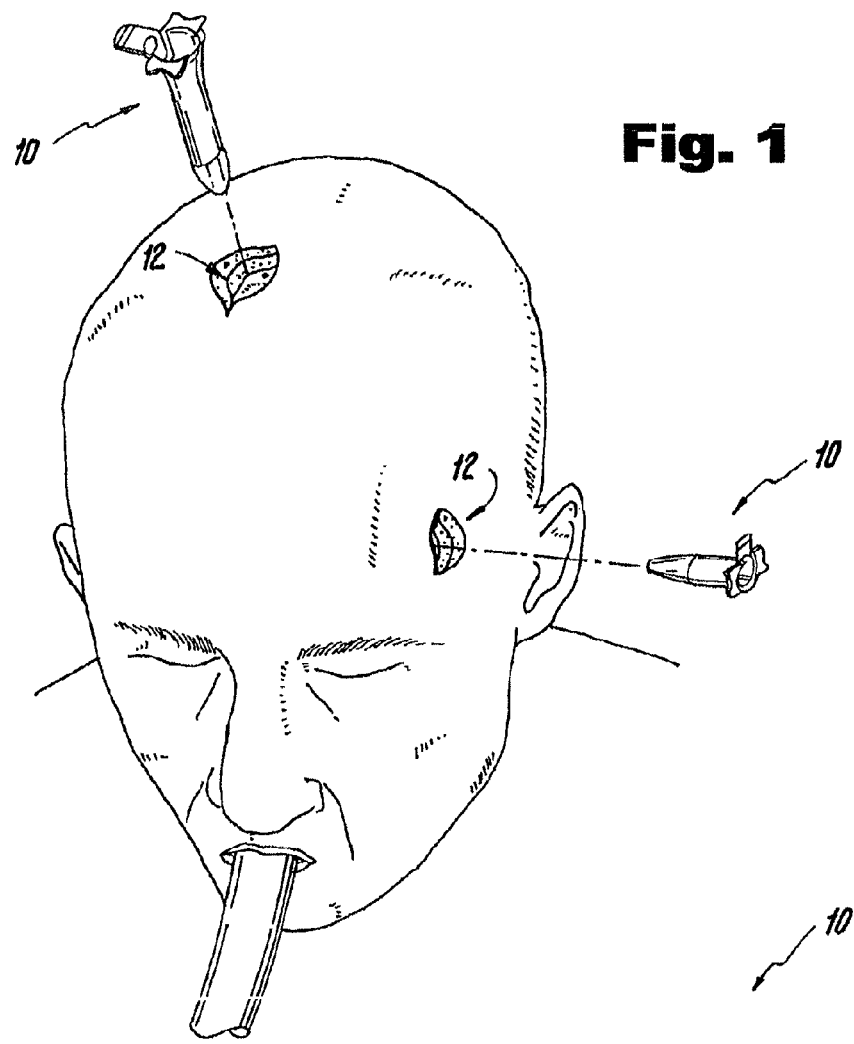
FIG. 1 is a view of a patient with a retractor assembly and a buttress channel positioned adjacent to a top of the head and lower skull.

This disclosure relates to a surgical instrument assembly and system for use with delicate tissues and methods of using the instrument assembly. The instruments are designed for use during surgery on delicate tissues, such as brain and breast tissues, although they may be used in any medical context. The instrument assembly includes several portions, such as, an introducer portion, a tissue access channel retractor portion ("channel portion") having at least one handle portion, and a stylette portion. These instrument portions are formed to maximize the surface area of the retractor, which distributes pressure approximately equally though out the surrounding tissues and minimizes effective localized retraction pressure on the tissues in contact or immediately surrounding the instrument.

In one embodiment, the surgical instrument assembly can be a retractor in the form of an arch or arc shape, into which an arch or arc shaped wedge introducer may be inserted for surgical access to the external portions or surfaces of the brain.

In another embodiment, the surgical instrument assembly can be a retractor in the form of a wedge with a tapered elliptical cross sectional shape, into which a tapered elliptical cross sectional introducer may be inserted for surgical access to the external portions or surfaces of the brain.

Alternatively, the external retractor and wedge introducer may be used to insert medical/cosmetic devices into or under delicate tissues.

The surgical instrument assembly system may also employ the external retractor as an external brain support buttress channel portion to lift the brain mass upward with respect to the cranium to provide stability and prevent the gelatinous brain materials from shifting during surgery. In the capacity of a brain support buttress channel portion ("buttress portion") also provides improved visualization and improved access to the surgical area by lifting the brain matter upward in the cranium.

The formation of the instrument assembly also eliminates the need to "pull" a retractor against tissue to clearly visualize the surgical area by initially providing a sufficient work area via the channel retractor. The use of the tissue access channel retractor portion of the instrument assembly eliminates or greatly lowers the possibility of accidental over-retraction. By avoiding excess retraction, damage to the surrounding tissues is also avoided, including possible brain damage.

While other closed curve configurations may be used, the preferably elliptical or arch shaped architecture formation of the instrument assembly portions is such that medical staff is afforded binocular vision, rather than the monocular vision typically found in similar devices. This elliptical architecture also provides far greater clearance for lighting access to illuminate the target surgical area and allows full visualization of that area. The forward edge of the channel retractor is preferably tapered to gently separate tissue to obtain a surgical area and minimizes disruption of the tissue.

The surgical instrument assembly system may also be useful as an inserter instrument for breast implants.

The dimensions of the surgical instrument assembly may vary and be modified according to an intended use. Generally, the surgical work space formed by the introducer portion 40 can have diameters of in the range of approximately 10 millimeters ("mm") to approximately 100 mm, and more typically in the range of approximately 25 mm to approximately 75 mm in its closed configuration. The open configuration of the introducer portion 40 may extend the diameter of the distal end 42 of the introducer portion 40 several millimeters, and may generally be determined by amount of extension desired by the surgical team during use as it is introduced into the lumen 22 of the retractor 20, and may include a flexible band portion to enhance its flexibility. The open configuration may also be determined by the overall desired circumference and diameter of the surgical instrument assembly for a particular use and may be manufactured in a variety of useful sizes to be available as is practical. The Surgical instrument assembly may be formed of any biocompatible material which will provide sufficient stability and strength necessary to provide a surgical work area. The biocompatible material may be disposable or sterilize-able for repeated use. In one embodiment, the surgical instrument assembly may be formed of a lightweight plastic material for ease of manipulation and/or the material may be transparent to allow direct visualization of underlying brain tissue thorough the instrument assembly portions.

The surgical instrument assembly system also enables integration with stereotactic neuro-navigation computer guidance systems to enhance visualization of the surgical area of the brain.

FIG. 1 illustrates in diagrammatic fashion the surgical instrument assembly system 10 adjacent a surgical aperture in the cranium of an intubated patient. An external retractor system 100 is also spaced from the lower skull, and will be described later in the specification.

Figure 2:
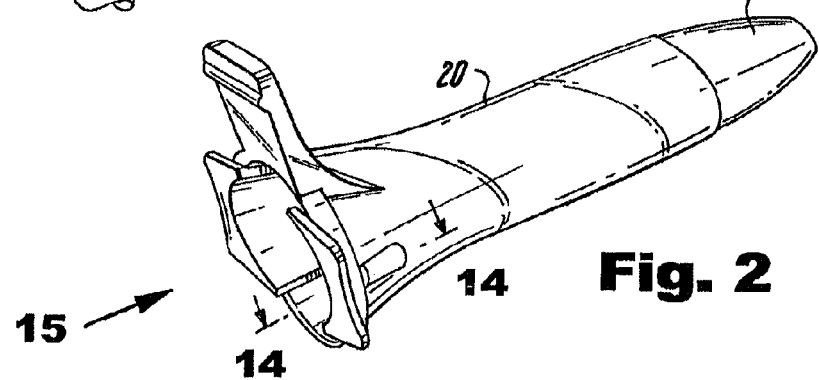
FIG. 2 is a perspective of retractor assembly of FIG. 1.

FIG. 2 is an enlarged perspective view of the surgical instrument assembly system 10 as shown in FIG. 1. The instrument assembly system 10 is comprised of two components, a retractor 20, and an introducer 40.

FIG. 3 illustrates the relationship of introducer 40 to retractor 20, prior to assembly. It is desirable that the introducer is easily fixed to and removable from the retractor both prior to and during the surgical procedure.

As also shown in FIG. 3, the surgical instrument assembly system may be formed by any method, including injection molding, as a single piece, or may be formed of two or more pieces which are permanently fixedly attached to each other. The distal end 42 of the introducer portion 40 is preferably a solid, rounded cone shape which may or may not include an opening 52 to the surrounding tissues as opposed to a cannula structure which always provides a distal opening. The distal end 42 preferably includes a gently increasing circumference 54, which increases and expands towards the proximal end 56 of the introducer portion 40. The introducer portion 40 has a main body 50, and may be divided into two approximate handle halves 46, having V-shaped cutouts 48 between the handle halves. The halves of the proximal end 56 are an integral unit, the term "halves" is used as a descriptor only and does not describe separable parts, as opposed to two disassemblable halves. The proximal end 56 may include at least one handle portion 46 which extends outwardly at an angle of approximately 90 degrees. A handle portion 46 may be useful to allow a medical team member to physically insert, manipulate or hold the handle portion 46, or a conventional surgical fixation cable may be attached to the handle portion 46. At least one of the handle portions 46 include at least one indentation or tab 44 to accept or snap into an additional portion of the surgical instrument assembly 10.

FIGS. 4-8 show a variety of views of the retractor portion 20 of this disclosure, including retractor 20 having a hollow working channel 22 and handle 28. The retractor 20 is generally formed to dimensions and shapes to coincide with the introducer portion 40 that may be slideably inserted into the brain access work channel 22 of the retractor portion 20. The retractor portion 20 is generally shorter in length than the introducer portion 40 to allow the distal end 42 of the introducer portion 40 to interact with the surrounding tissues. As best seen in FIGS. 6 and 7, the retractor portion 20 is formed as a hollow elliptical rounded wedge 21 having a tapered distal leading edge 24. The proximal edge of the retractor 20 includes a slightly rounded lip 26 and a handle portion 28. At least one hole 30 is formed in wedge 21, just distal of lip 26. Hole 30 will positively align with tab 44 of introducer 40 to prevent or inhibit unnecessary movement or slipping of the instrument assembly components best seen in sectional view FIG. 15. The handle portion 28 allows the retractor portion 20 to be fixed in space with the use of a standard or conventional neurosurgical fixation cable device or clamp 58.

Figure 9:
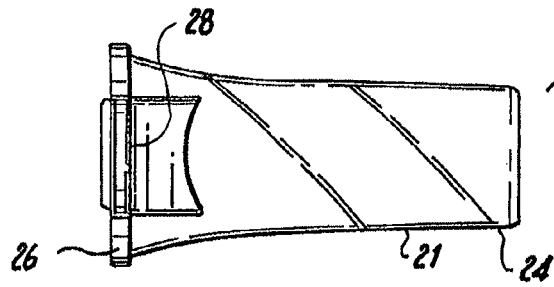
FIG. 9 is a top plan view thereof.
Figure 10:
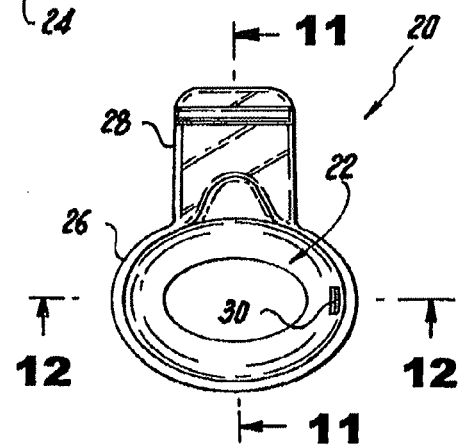
FIG. 10 is a proximal end view of the retractor.
Figure 11:
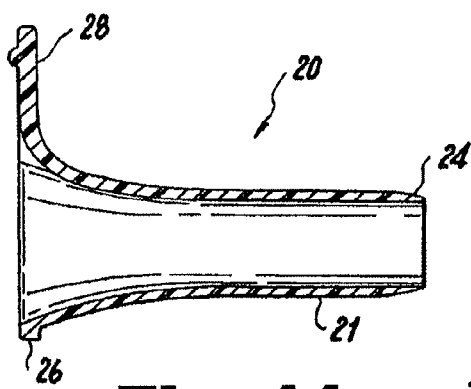
FIG. 11 is a side sectional elevation thereof.
Figure 12:
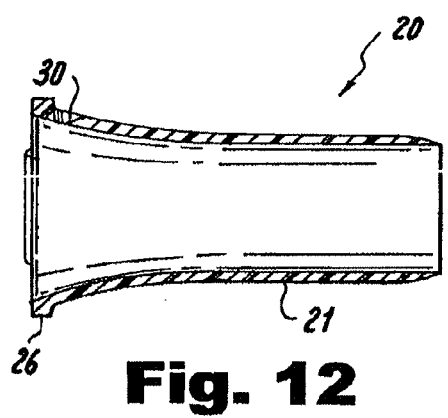
FIG. 12 is a top plan sectional view thereof.
Figure 13:
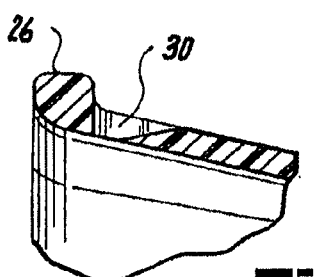
FIG. 13 is a sectional detail view of the groove, taken from FIG. 12.
Figure 14:
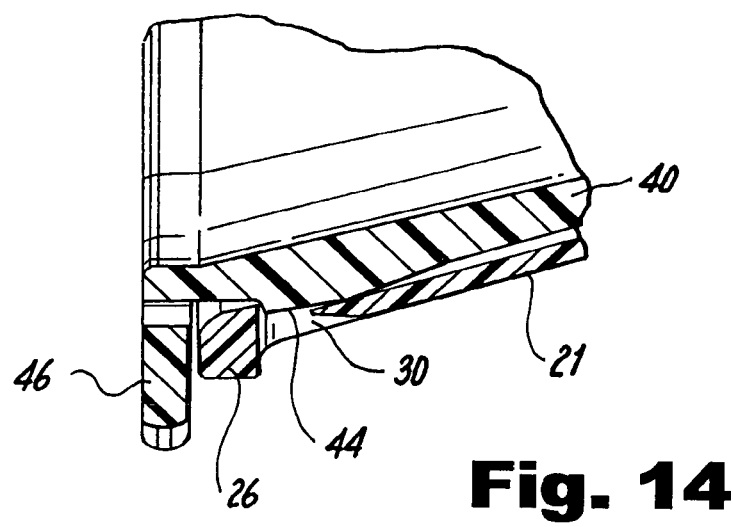
FIG. 14 is a sectional detail of locking tab and groove, taken at 14-14 of FIG. 2.

FIG. 9 illustrates a side view of a retractor 20, having a proximal lip 26 of the surgical instrument assembly and optionally having a handle portion 28 perpendicular to the proximal lip 26; and the hollow elliptical rounded wedge 21 portion of the retractor 20 extends to the rounded distal end 24. FIG. 10 is a frontal view of the retractor 20, showing the lumen 22 and the handle portion 28. FIG. 11 is a cross-sectional view of the retractor 20 of the rounded shape of the retractor 20 to avoid damage to brain tissues. FIG. 12 is a top plan view of the retractor 20, emphasizing the groove like cut-out hole 30 which can allow the introducer 40 to integrally fit and temporarily lock/snap into hole 30, thereby causing both the retractor 20 and introducer 40 to function as one, while desired by the medical team. FIG. 13 is an enlarged view of the grooved hole 30. FIG. 14 is a cross-sectional view of the tab 44 of the introducer 40 while it is engaged within the grooved hole 30 of the retractor 20.

Figure 15:
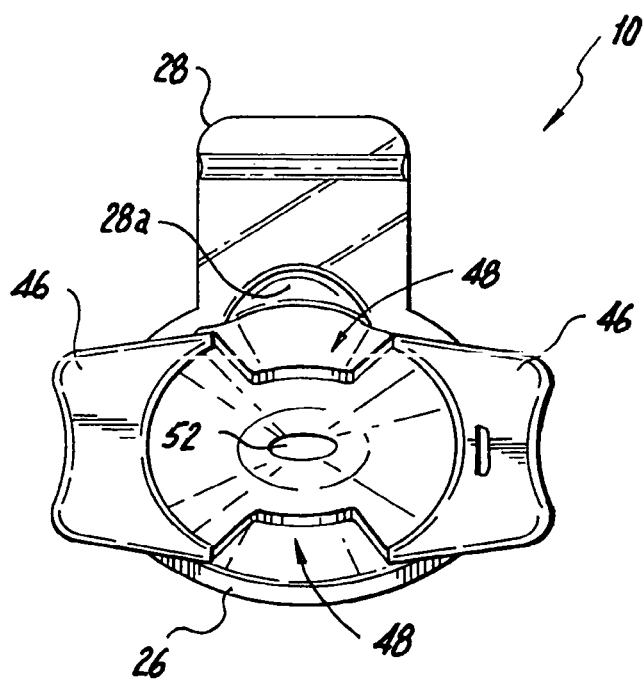
FIG. 15 is a proximal end view of the assembly, taken at arrow 15 in FIG. 2.

Shown in FIG. 15 is a proximal end view of assembled instrument where the handle portions 46 overlying lip 26 of retractor 20, and V-shaped cutouts 48 residing in lumen 22. Handle 28 of retractor 20 is molded integral with lip 26, providing both rigidity and strength. FIG. 15 also shows that where a base of handle 28 is attached to retractor 20, handle 28 may optionally merge in a cascading shaped dip 28a, interrupting the continuous curve of the proximal end of hollow retractor 20. Such a cascading dip 28a allows for easier finger access into the working channel of hollow retractor 20.

Figure 16:
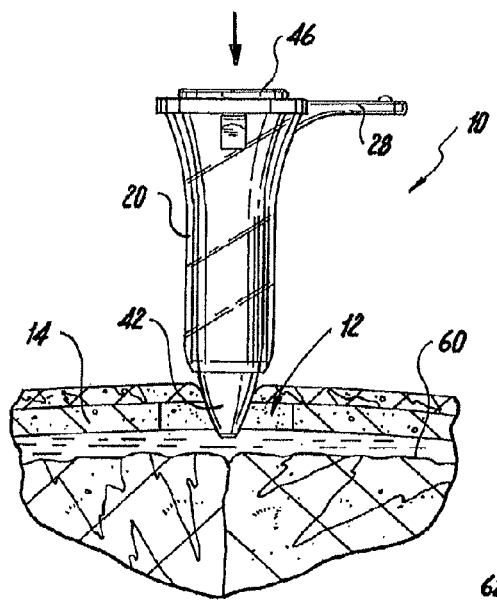
FIG. 16 is a view of the instrument assembly being inserted into the top of a skull.
Figure 17:
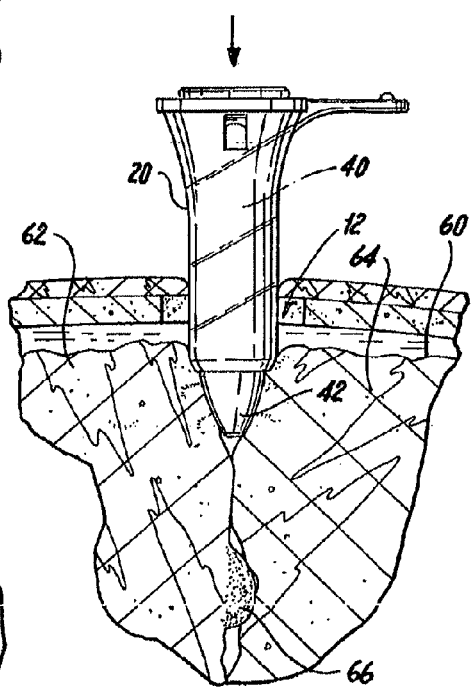
FIG. 17 is a view of the instrument assembly spreading the brain lobes apart.
Figure 18:
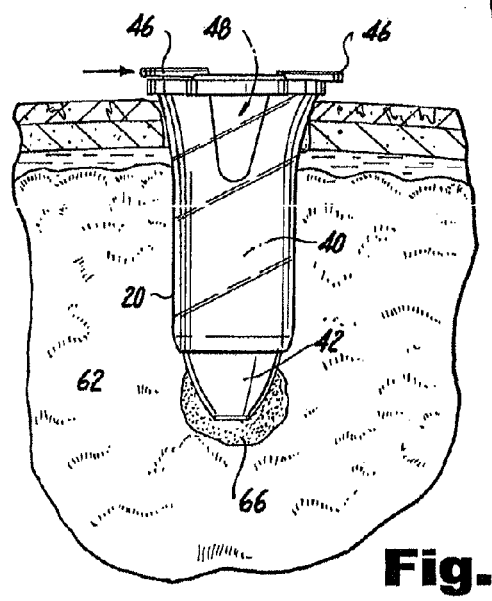
FIG. 18 is a view of the instrument assembly installed, taken at arrows 18-18 of FIG. 17, with an ear of introducer flexed.
Figure 19:
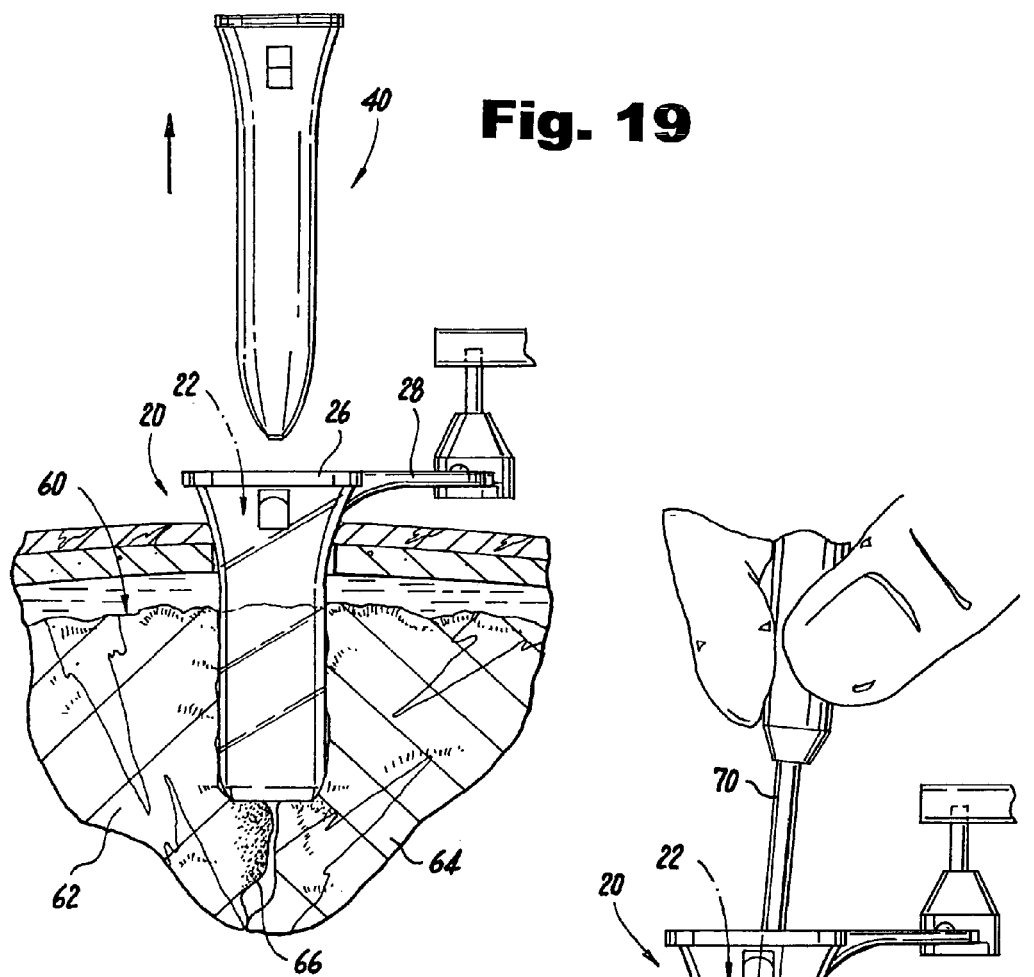
FIG. 19 is a view of the instrument assembly with the introducer removed.
Figure 20:
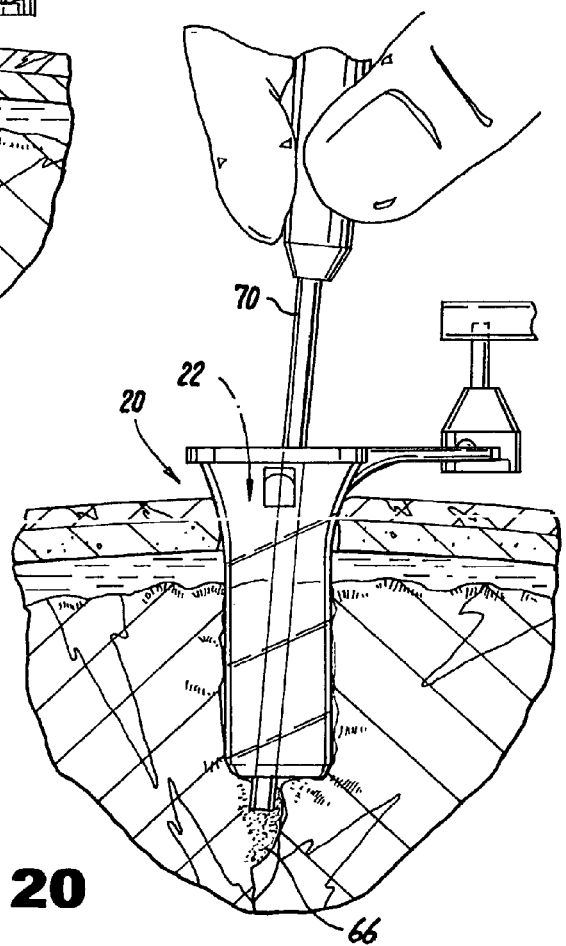
FIG. 20 is a view of surgical instruments within the retractor channel.

FIGS. 16-20 illustrate diagrammatically the method if installing surgical instrument assembly 10 into the aperture 12 in cranium 14. As seen in FIG. 16, instrument assembly 10 is inserted into aperture 12. Distal end 42 of introducer 40 is abutting brain tissue 60. As Instrument assembly 10 is introduced, distal end 42 of introducer 40 begins to spread tissue or lobes 62 and 64 of brain 60, as shown in FIG. 17. FIG. 18 is an elevational.view of the installed surgical instrument assembly 10, taken along arrows 18-18 of FIG. 17. Upon installation, handles 46 of introducer 40 may be flexed inward, thereby releasing the hole 30 of retractor 20 from the tab 44 of introducer 40. FIG. 19 illustrates introducer 40 during removal from lumen 22 of retractor 20. FIG. 20 shows surgical instruments 70 within lumen 22 of retractor 20, examining brain tissue 60.

Figure 21:
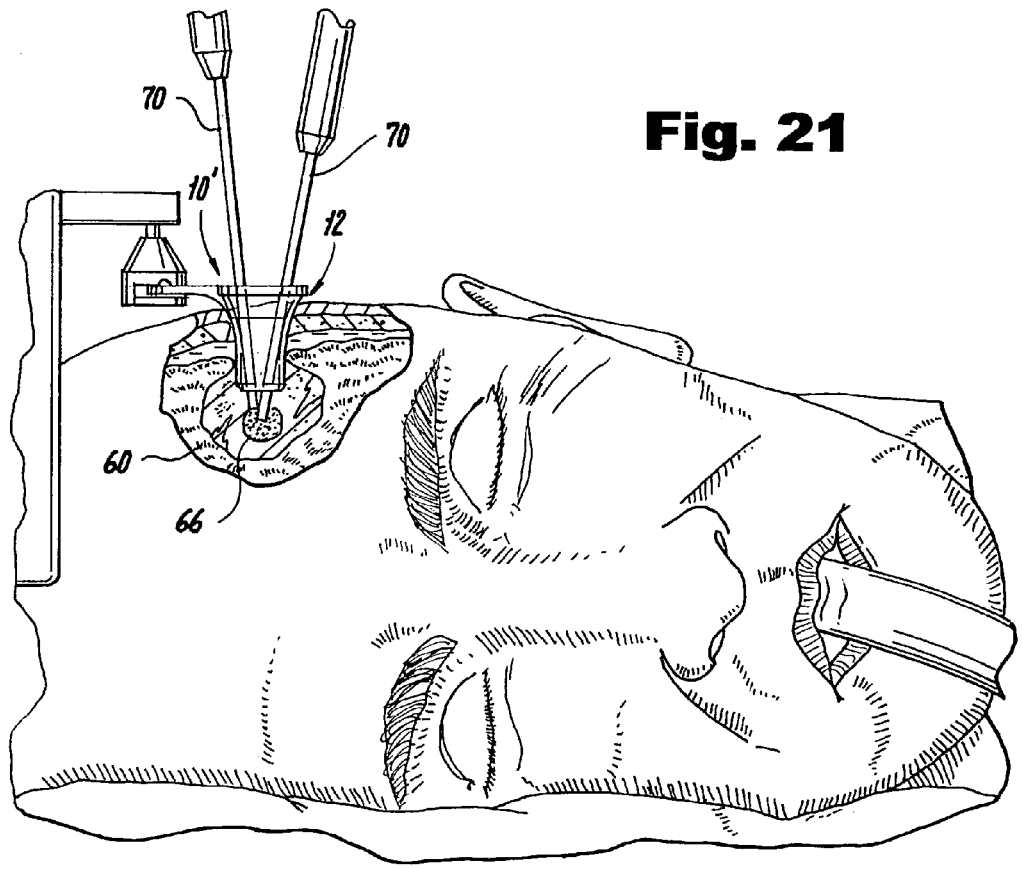
FIG. 21 is a diagrammatic sectional view of an embodiment which is installed transversely into tissue.
Figure 22:
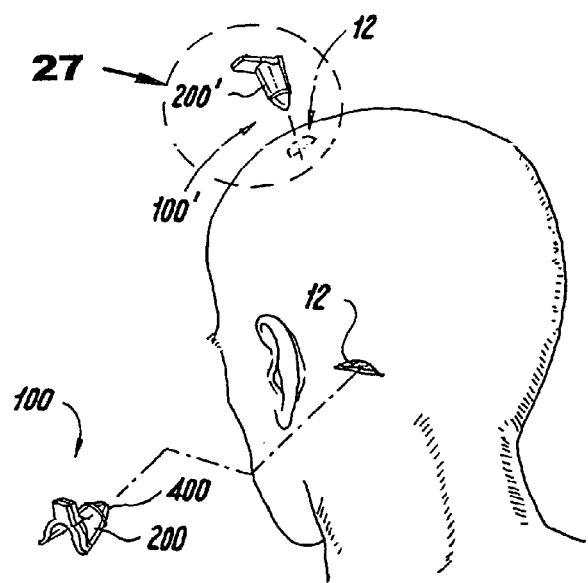
FIG. 22 is a view of the external instrument assembly system adjacent to the lower skull.

FIG. 21 is a diagrammatic perspective view of an embodiment of the surgical instrument assembly 10, adjacent an aperture 12 located at the temple region of a patient's cranium 14. In this embodiment, the overall length of surgical instrument assembly 10 is sufficient to transversely penetrate the cranium and brain tissue 60. Surgical instrument assembly 10 is shown installed in FIG. 22.

Figure 23:
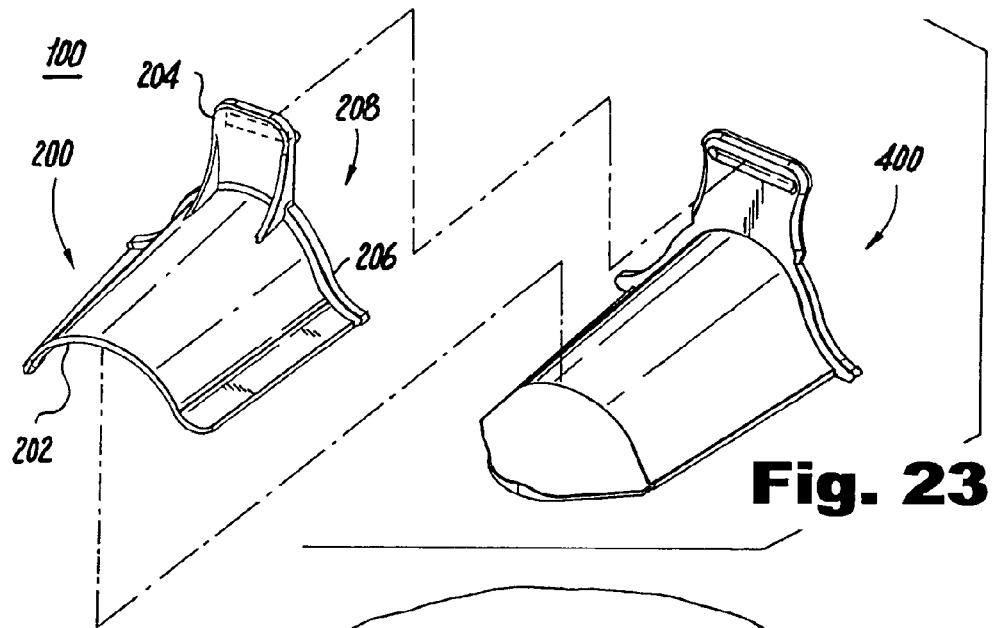
FIG. 23 is a view of the instrument assembly components of FIG. 22 exploded.
Figure 24:
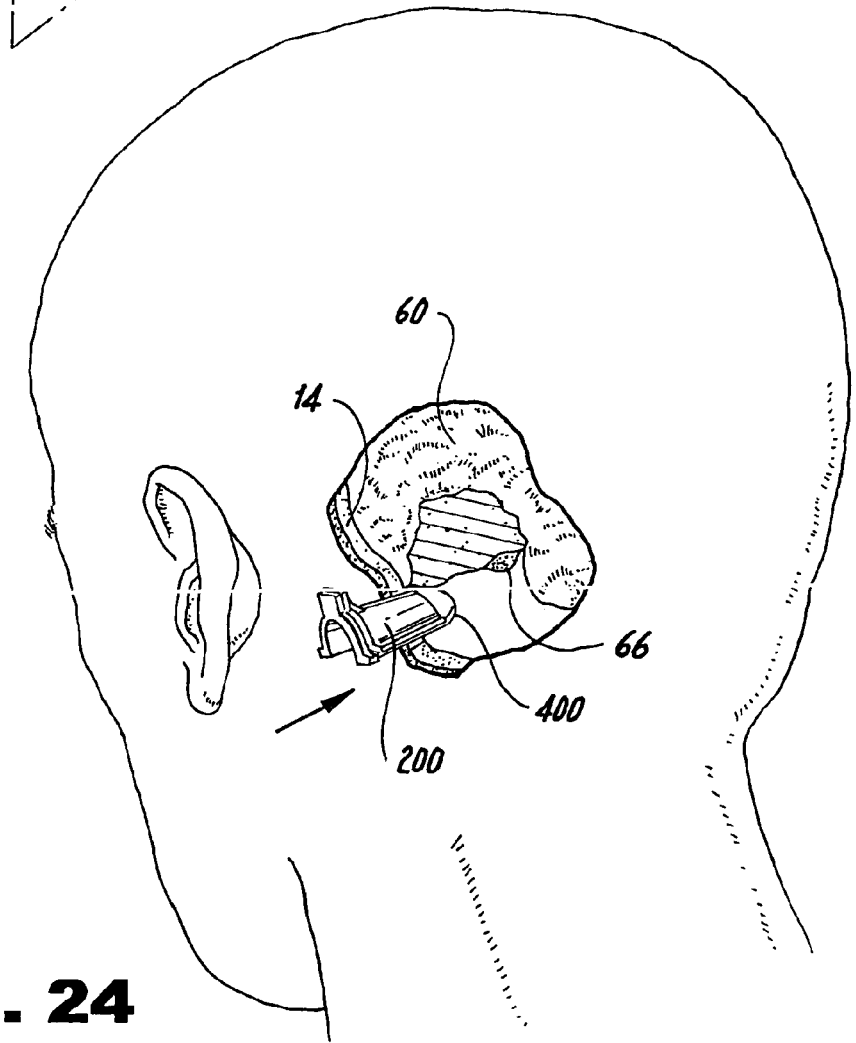
FIG. 24 is a perspective view of the instrument assembly system installed in the lower skull.

FIG. 23 is a perspective view of the external retracting buttress channel 100. External buttress channel instrument assembly 100 is comprised of buttress channel component 200, and wedge introducer component 400. External buttress channel component 200 has a generally arched, hemi-elliptical architecture, where it is wider along the base than it is tall or high. The buttress channel component 200 includes a smooth, tapered leading edge 202. A handle fixation member 204 is approximately perpendicular to the rounded lip 206 of the proximal end 208. The handle member 204 may be employed as an attachment point to a standard neurosurgical armature fixation device. The external buttress channel component 200 may be used to lift, support or manipulate the brain within the skull cavity to provide additional or improved vision of the surgical area, as seen in FIG. 24.

Also seen in FIG. 23 is the external wedge introducer portion 400 for the external buttress channel component 200. Buttress channel 200 is designed to gain access to external structures along, around or beneath the brain by elevating the surfaces of the brain to allow access to surgical locations on or near the surface of the brain tissues. In operation, prior to insertion, introducer portion 400 is attached to buttress channel 200 such that sloping distal end 402 protrudes from the distal open end 210 of buttress channel 200. This pushes away brain tissue at the outer brain surface 66 gently during insertion. After insertion, introducer portion 400 is withdrawn to leave a working channel of decreasing hemi-oval cross section from proximal end 208 to distal end 210. Radial surface of buttress channel 200 supports the outer surface 66 of the brain tissue 60, best seen in FIG. 24. Note that surface of wedge introducer 400 conforms to the inside of buttress channel surface; proximal end 208 and handle member 204 conform to proximal end 406 and fixation member 408 of introducer 400 respectively. Fixation member 204 of buttress channel 200 is designed to be attached to a standard neurosurgical armature fixation device.

Figure 25:
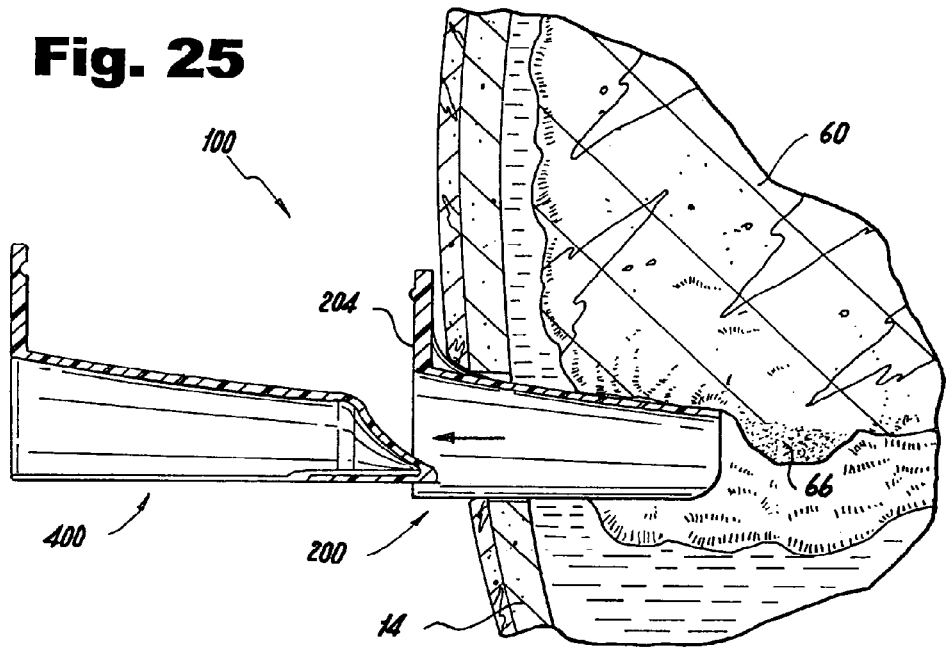
FIG. 25 is a diagrammatic side section of installed instrument assembly, with the introducer removed.
Figure 26:
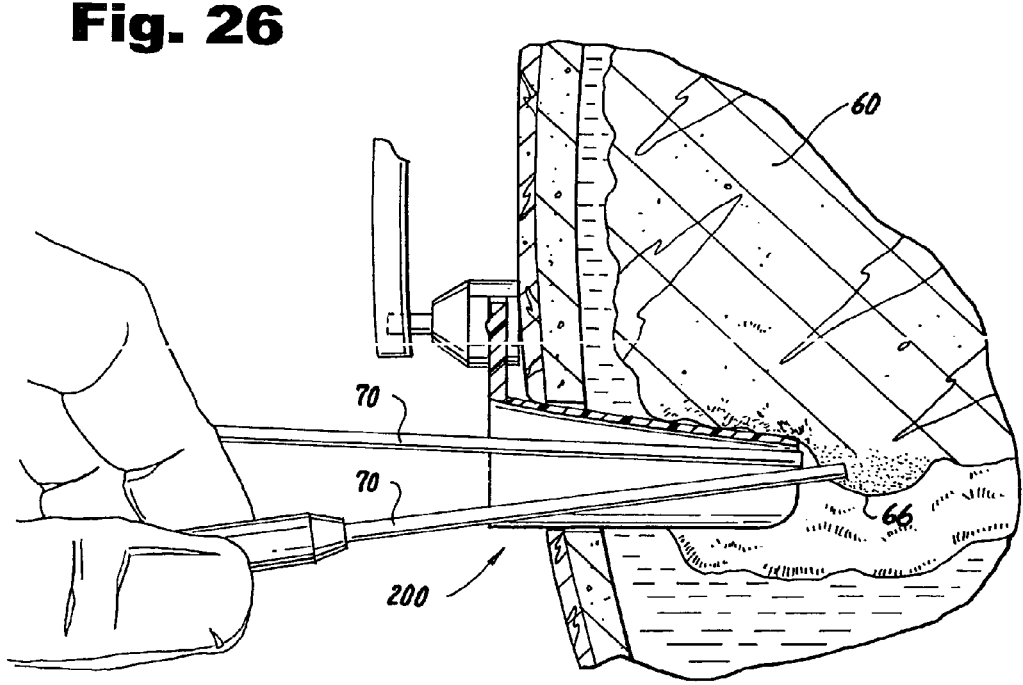
FIG. 26 is a diagrammatic view of the instruments working on an external tumor.

FIGS. 25 and 26 are diagrammatic view of the instruments working on an external tumor, where the further surgical instruments 70 are inserting into the operating space formed by the instrument assembly system to allow the surgical team to work on the tissues as necessary.

Figure 27:
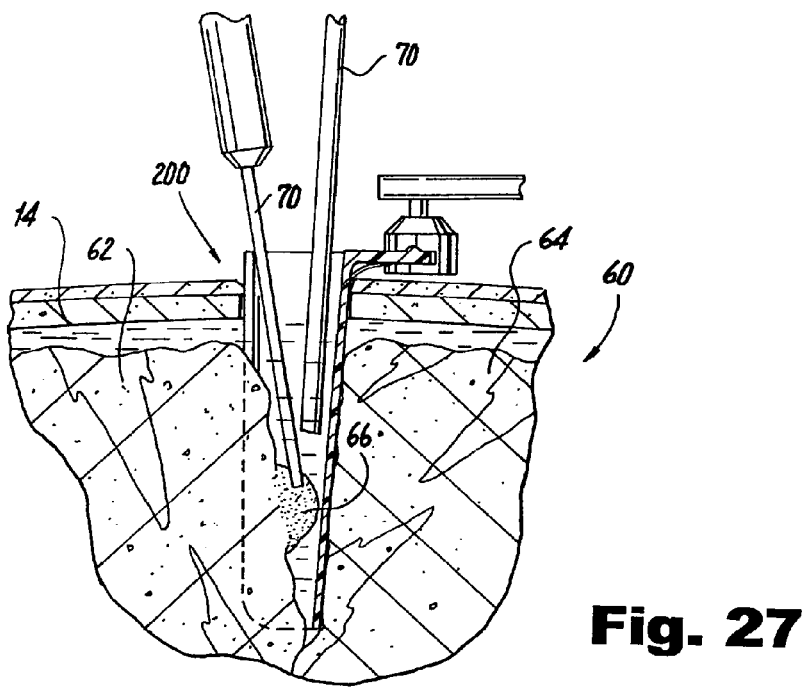
FIG. 27 is a diagrammatic view of an alternative embodiment, installed through forehead.
Figure 28:
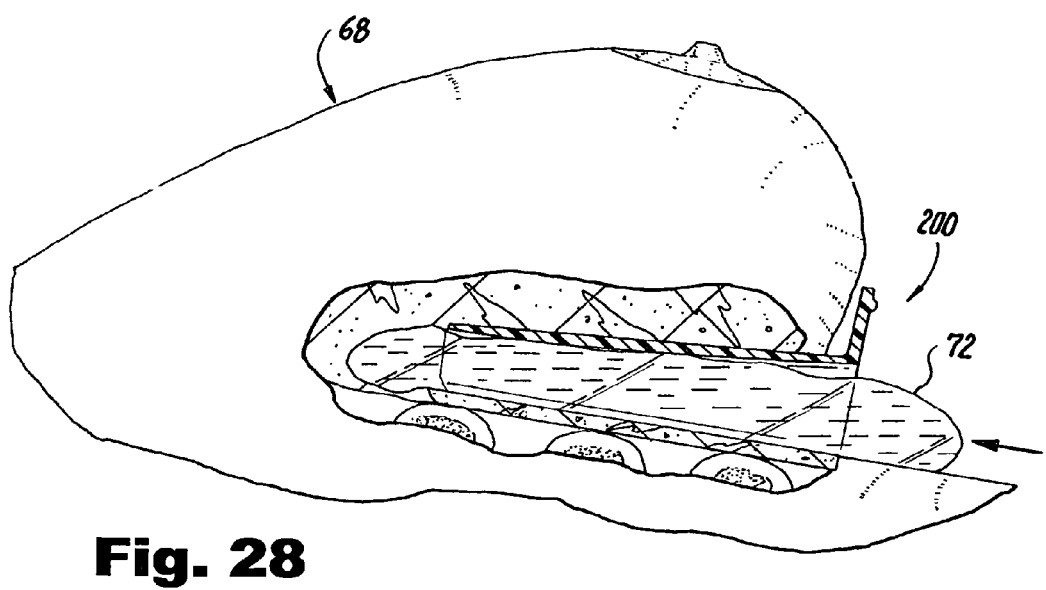
FIG. 28 is a diagrammatic view of the instrument assembly installed into breast tissue.

FIG. 27 is a diagrammatic view of an embodiment, which may be installed through the forehead as necessary for surgical procedures. FIG. 28 is a diagrammatic view of the instrument assembly installed into breast tissue 68, where it may be used for insertion of implants 72 and the like.

FIG. 28 shows use of an arched buttress channel 200 and wedge introducer component 400 which may be used, for example, for access to brain tissue or for inserting an inflatable prosthesis into breast tissue.

Figure 29:
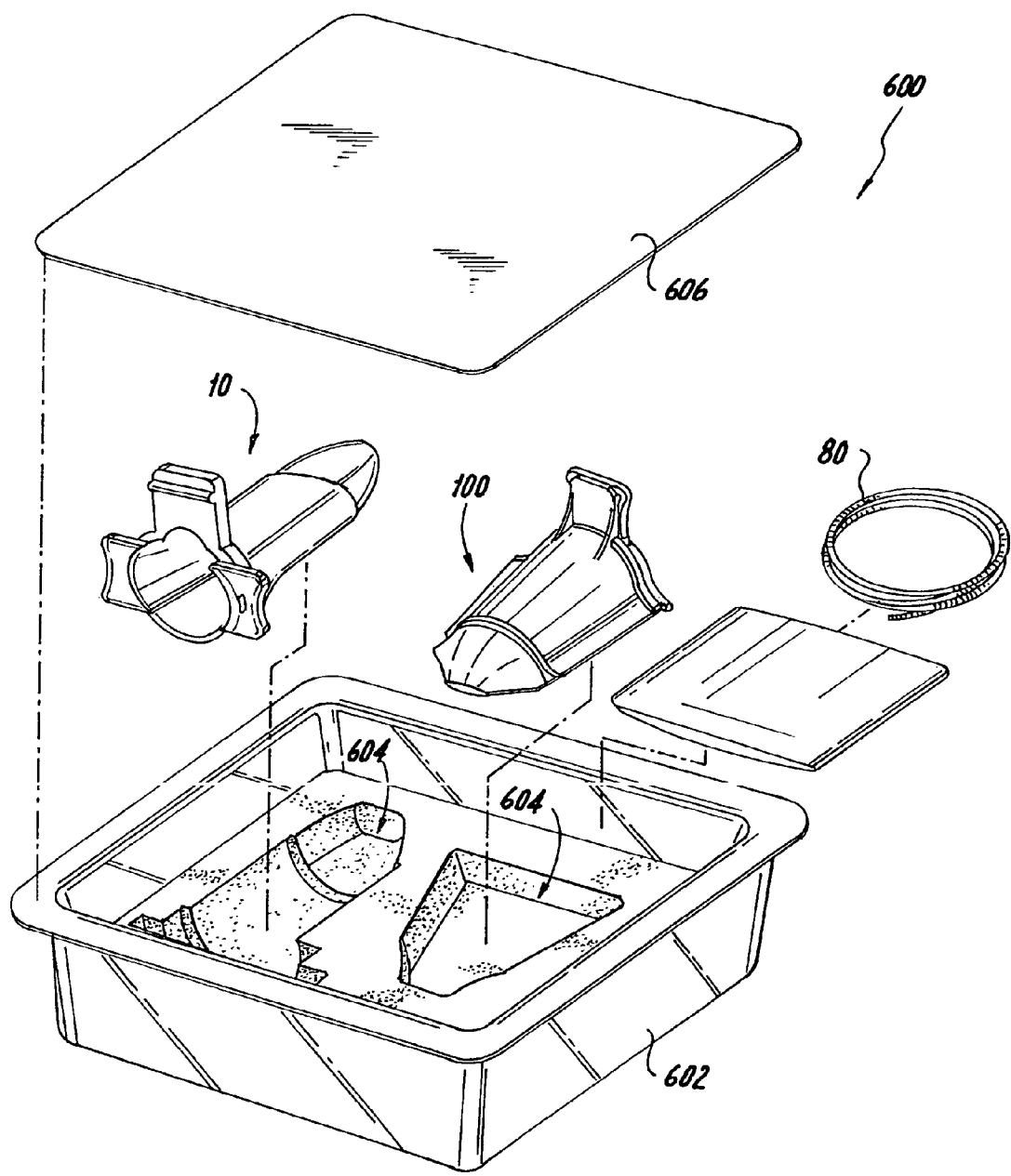
FIG. 29 is a perspective exploded view of a surgical kit.

FIG. 29 is a perspective exploded view of a surgical kit. The Kit 600 includes an injection-molded or vacuum-formed housing 602, providing cavities 604 to receive components of the surgical instrument assembly system 10 and the external retracting buttress channel system 100. A stylette 80 may also be included. Upon placement of all desired components within the housing 602, the sterile kit will be sealed with a Tyvek sheet 606. Upon removal of sheet 606 by the surgeon, the sterile components of kit 600 can be utilized and employed as required in a surgical operation.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. A surgical apparatus comprising:
   a retractor comprising a first hollow sleeve extending along a longitudinal axis from a proximal retractor end to a distal retractor end, the first hollow sleeve comprising an enclosed channel having a cross-sectional retractor shape, with respect to a plane perpendicular to the longitudinal axis, that is elliptical or oval;
   an introducer comprising a second hollow sleeve extending from a proximal introducer end to a distal introducer end, the second hollow sleeve comprising an oval lumen and being configured to selectively and removably install within the first hollow sleeve with an extended portion of the introducer extending beyond the distal retractor end, wherein the extended portion of the introducer is tapered to generally increase in size from the distal introducer end to a location adjacent the distal retractor end, has a cross-sectional introducer shape, with respect to a plane perpendicular to the longitudinal axis, that is elliptical or oval, and wherein at least a portion of the extended portion of the introducer has a rounded profile in a plane parallel to the longitudinal axis to displace brain tissue transversely to the longitudinal axis without damage to the brain tissue;
   wherein the retractor is transparent at least at a first transparent region between the distal retractor end and the proximal retractor end; and
   wherein the introducer is transparent at least a second transparent region between the distal introducer end and the proximal introducer end; and
   wherein the first transparent region and the second transparent region overlap to allow direct visualization of brain tissue through both the retractor and the introducer.

2. The surgical apparatus of claim 1, wherein the introducer is transparent at least at the extended portion of the introducer.

3. The surgical apparatus of claim 1, wherein, upon insertion of the surgical apparatus into brain tissue, the distal introducer end forms a surgical work space having a width of about 10 millimeters to about 100 millimeters.

4. The surgical apparatus of claim 1, wherein, upon insertion of the surgical apparatus into brain tissue, the distal introducer end forms a surgical work space having a width of about 25 millimeters to about 75 millimeters.

5. The surgical apparatus of claim 1, wherein the extended portion of the introducer comprises a rounded cone.

6. The surgical apparatus of claim 1, wherein the distal introducer end comprises an opening therethrough.

7. The surgical apparatus of claim 6, wherein the opening is Oval.

8. The surgical apparatus of claim 6, wherein the opening is elongated in a direction perpendicular to the longitudinal axis.

9. The surgical apparatus of claim 6, wherein the oval lumen comprises a surgical work space that expands from a first size at the opening to a second, larger size at the proximal introducer end.

10. The surgical apparatus of claim 9, wherein the surgical work space is sized to be used in conjunction with working surgical instruments and the opening is sized to allow for removal of tissue from a surgical site adjacent the opening.

11. The surgical apparatus of claim 1, wherein the retractor comprises a rigid handle that, when attached to a surgical clamp, fixes the first hollow sleeve in space with respect to the brain tissue.

12. The surgical apparatus of claim 1, wherein the first hollow sleeve is tapered, along at least a portion of its length, to have a larger exterior size at the proximal retractor end and a smaller exterior size at the distal retractor end.

13. The surgical apparatus of claim 12, wherein the first hollow sleeve is dimensioned to permit simultaneous access for a plurality of working surgical instruments to a surgical site adjacent the distal retractor end when the introducer is removed from the retractor.

14. The surgical apparatus of claim 1, wherein the introducer and the retractor have corresponding locking features adapted to temporarily secure the introducer to the retractor.

15. The surgical apparatus of claim 14, wherein the locking features comprise at least two opposed lock members that are resiliently biased away from one another to engage the introducer with the retractor, and that are released by squeezing the at least two opposed lock members towards each another.

16. The surgical apparatus of claim 15, wherein the locking features comprise one or more protrusions formed on an exterior surface of the introducer and one or more corresponding detents formed on an interior surface of the retractor, the one or more protrusions being engaged with the one or more detents when the introducer is fully inserted in the retractor.

17. The surgical apparatus of claim 16, wherein one or more cutouts divide the proximal introducer end into first and second handles that are movable with respect to one another to thereby form the at least two opposed lock members.

18. The surgical apparatus of claim 1, wherein a portion of a perimeter of the first hollow sleeve at the proximal retractor end comprises a cascading dip.

* * * * *